United States Patent [19]

Golborn et al.

[11] 4,053,450

[45] Oct. 11, 1977

[54] DIALKYL ALKYL AND CYCLIC PHOSPHORAMIDOMETHYL PHOSPHONATES

[75] Inventors: Peter Golborn, Skelmersdale, England; James J. Duffy, Buffalo, N.Y.

[73] Assignee: Hooker Chemicals & Plastics Corporation, Niagara Falls, N.Y.

[21] Appl. No.: 755,884

[22] Filed: Dec. 30, 1976

Related U.S. Application Data

[60] Division of Ser. No. 618,720, Oct. 1, 1974, Pat. No. 4,018,560, which is a continuation of Ser. No. 438,481, Jan. 31, 1974, abandoned, which is a continuation-in-part of Ser. No. 239,799, March 30, 1972, Pat. No. 3,812,218.

[51] Int. Cl.$^2$ .................................................. C08K 5/51
[52] U.S. Cl. ........................ 260/45.8 R; 260/45.9 NP
[58] Field of Search .................. 260/45.8 R, 45.9 NP

[56] References Cited

U.S. PATENT DOCUMENTS 3,966,478  6/1976  Toy et al. .................... 760/45.9 NP

*Primary Examiner*—V.P. Hoke
*Attorney, Agent, or Firm*—P. F. Casella; W. J. Crossetta

[57] ABSTRACT

New compounds are disclosed of the formula:

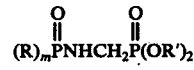

wherein R' is phenyl, lower alkenyl and halogen substituted and unsubstituted lower alkyl of 1-6 carbon atoms, $m$ is an integer from 1-2 wherein when $m$ is 2, R is alkoxy of 1-8 carbon atoms and when $m$ is 1, R is alkylene dioxy of 2-8 carbon atoms. The compounds of this invention are useful as flame retardant agents for textile materials and in the production of polymers and copolymers which possess flame retardant properties.

12 Claims, No Drawings

DIALKYL ALKYL AND CYCLIC PHOSPHORAMIDOMETHYL PHOSPHONATES

This is a division, of application Ser. No. 618,720, filed Oct. 1, 1975 now U.S. Pat. No. 4,018,560 which is a continuation of Ser. No. 438,481, filed Jan. 31, 1974, now abandoned which is a continuation-in-part of Ser. No. 239,799, filed Mar. 30, 1972, now U.S. Pat. No. 3,812,218.

FIELD OF INVENTION

This invention relates to novel compounds of the formula

wherein R' is phenyl, lower alkenyl and halogen substituted and unsubstituted lower alkyl of 1-6 carbon atoms, m is an integer from 1-2 wherein when m is 2, R is alkoxy of 1-8 carbon atoms and when m is 1, R is alkylene dioxy of 2-8 carbon atoms. The invention includes methods of applying the above novel compounds to normally flammable textiles and thermoplastic, thermosetting and elastomeric resin compositions so as to render them flame retardant.

BACKGROUND OF THE INVENTION

Many flame retarding agents and methods of application have been developed in attempts to obtain flame resistant textile materials and thermoplastic resin compositions.

Flame retardant textiles have been produced by depositing metal oxides, within or on the textile fibers, by the successive precipitation of ferric oxides and a mixture of tungsten acid and stannic oxide or by successive deposition of antimony trioxide and titanium dioxide. Such processes require plural treatment baths in which strongly acidic solutions are employed thus posing the problem of possible textile degradation. Furthermore, metal oxide coatings on textile materials create difficulties in subsequent dyeing processes which deleteriously affect the hand of the finished product. Another process involves the use of a single processing bath wherein a dispersion of a chlorinated hydrocarbon and finely divided antimony oxide is padded on the textile material. Near the textile combustion temperature antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen ortho-phosphate. Textile products so treated however are subjected to metathesis reaction with cations during washing, and must be regenerated by reacting the wash product with an ammonium chloride solution.

The production of thermoplastic resin compositions which are flame retardant is of considerable commercial importance. For example, such articles as castings, moldings, foamed or laminated structures and the like are required, or are at least desired, to be resistant to fire and flame and to possess the ability to endure heat without deterioration. The use of various materials incorporated into thermoplastic resins so as to improve the flame retardancy thereof has been known. Many compounds have been commercially available for such use, among them being chlorostyrene copolymers, chlorinated paraffin wax in admixture with triphenyl styrene, chlorinated paraffins and aliphatic antimonical compounds, as well as antimony oxide-chlorinated hydrocarbon mixtures. A problem associated with these compounds has been however, the fact that generally a large amount, i.e., upwards of 35% of additive, must be incorporated into the resin in order to make it sufficiently flame retardant. Such large amounts of additive may deleteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

OBJECTS OF THE INVENTION

It is, therefore, a principal object of this invention to provide novel compounds of the formula:

wherein R' is phenyl, lower alkenyl and halogen unsubstituted lower alkyl of 1-6 carbon atoms, m is an integer from 1-2 wherein when m is 2, R is alkoxy of 1-8 carbon atoms and when m is 1, R is alkylene dioxy of 2-8 carbon atoms. It is also an object of this invention to provide flame retarding textile materials comprising normally flammable cellulosic, proteinaceous or analogous man-made materials. Another object is to provide a method for treating normally flammable cellulosic, proteinaceous or analogous man-made materials to render them flame retardant. Another object is to provide flame retarding thermoplastic resin compositions comprising normally flammable thermoplastic resin materials. A further object is to provide a process for treating normally flammable thermoplastic resin compositions to render them flame retardant. A particular object is to devise a composition comprising normally flammable cellulosic, proteinaceous or analogous man-made materials and an effective flame retardant amount of the compound represented by the formula

wherein R, R' and m are as above described. A further particular object is to devise a composition comprising normally flammable thermoplastic polymer and an effective flame retarding amount of the before described novel compound.

These and other objects of the present invention will be obvious from the following description.

DESCRIPTION OF THE INVENTION

In accordance with this invention there are provided novel compounds, for imparting flame retardancy to textiles and thermoplastic, thermosetting and elastomeric resin materials of the formula:

wherein R' is phenyl, lower alkyl and halogen substituted and unsubstituted lower alkyl of 1-6 carbon atoms, m is an integer from 1-2 wherein when m is 2, R is alkoxy of 1-8 carbon atoms and when m is 1, R is alkylene dioxy of 2-8 carbon atoms. More specifically, the preferred compounds of the present invention include these compounds wherein R' is lower alkyl of 1-6 carbon atoms and m is 2.

Illustrative examples of compounds of the present invention include, for instance, compounds of the general formula such as

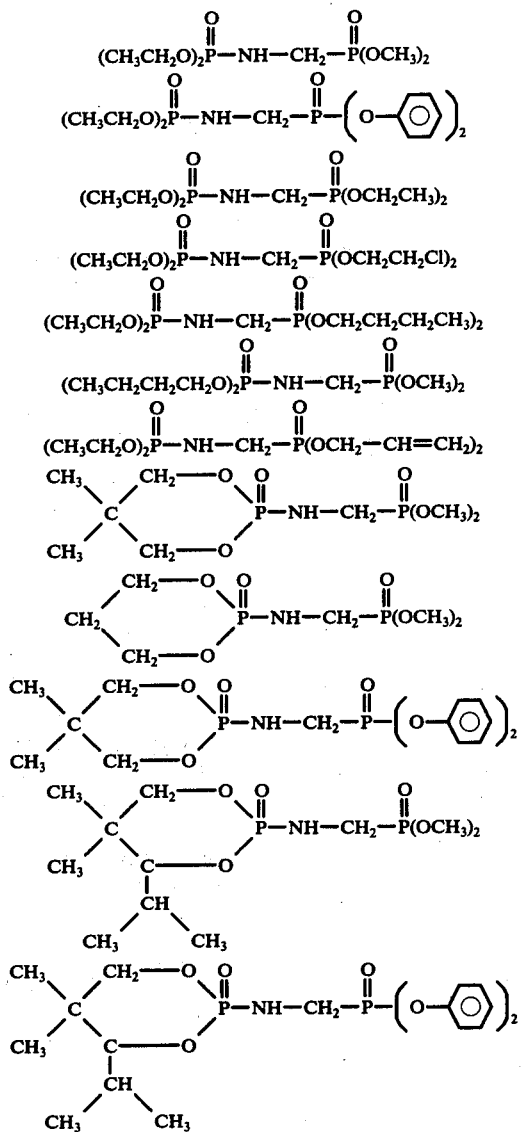

The synthesis of the compositions of the present invention is accomplished by reacting a N-hydroxymethyl phosphoramidate of the formula

with a trialkyl phosphite of the formula

wherein R, R' and m are as previously described neat, or in the presence of a suitable solvent, or in an excess of the phosphite. Preferably the reaction is carried out for about 1 to about 6 hours at a temperature of about 80° C to about 120° C. The solvent excess phosphite, or other volatile material, is thereafter stripped, under reduced pressure, or otherwise removed from the product. Suitable solvents include benzene, toluene, xylene, aliphatic, or aromatic hydrocarbons, glymes, diglymes, dimethyl formamide and the like. Typical N-hydroxymethyl phosphoramidate operable as reactants herein include

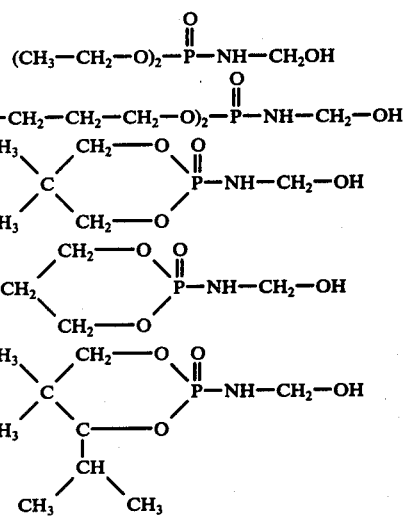

One or more of the novel compounds of this invention may be applied to textile materials by conventional finishing techniques such as by thermal pad curing so as to incorporate into the textile a flame retardant amount thereof. The compounds of this invention have advantages over the flame retardant agents of the prior art in that they may be used on a variety of textile materials of different chemical composition, and they may be applied by a variety of methods. They may be applied to materials in either the fiber or fabric form to give flame retarding materials with minimum detectable physical changes in the quality or hand of the textile material.

The products of this invention may be applied to cellulosic materials in several ways to give a durable flame retardant treatment. For example, the products of this invention may be reacted with formaldehyde to give N-hydroxymethyl derivatives which can react with cellulosic materials in a known manner. Alternatively aqueous mixtures of the products with formaldehyde, urea, trimethylol melamine or other known cellulose crosslinking agents may be applied to a cellulose substrate with the aid of an acidic catalyst by a pad dry process.

More preferably the N-hydroxymethyl derivative of the products of this invention prepared by the condensation of the products with formaldehyde, are mixed in an aqueous medium with trimethylol melamine and a Lewis acid catalyst such as $NH_4Cl$ or $Zn(NO_3)_2 \cdot 6H_2O$. The cellulosic material is immersed in an aqueous solution of the methylol derivative, trimethylol melamine, and $Zn(NO_3)_2 \cdot 6H_2O$ and squeezed on a two roll padder to 70–90% wet weight pick-up. The material is dried at 220°–270° F for 1–3 minutes and cured at 300°–370° F for 1–6 minutes in a circulating air oven. The samples are then washed in hot water and dried. The finished samples have a flame retardant add-on of about 40% and preferably about 10 to about 25% by weight.

The flame retardant agents of this invention may be applied to various textiles such as cellulosic or, proteinaceous materials. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs.

The flame retardant compounds or additives of the invention may be incorporated into thermoplastic resin compositions by any known method. That is to say, the flame retardant additive may be added to the resin by milling the resin and the additive on, for example, a two-roll mill, or in a Banbury mixer etc., or it may be added by molding or extruding the additive and resin simultaneously or by merely blending it with the resin in powder form and thereafter forming the desired article. Additionally, the flame-retardant may be added during the resin manufacture, i.e., during the polymerization procedure by which the resin is made, provided the catalysts etc. and other ingredients of the polymerization system are inert thereto. Generally, the compounds of this invention may be incorporated into the thermoplastic resin in flame-retarding amounts, i.e., generally amounts ranging from about 5% by weight, to about 50% by weight, preferably from about 20% by weight, to about 40% by weight, based on the weight of the polymer, have been found sufficient.

The resin systems embraced within the scope of this invention include the homopolymers and copolymers of saturated and unsaturated aliphatic, alicyclic, and aromatic hydrocarbons and their derivatives. Suitable monomers are ethylene, propylene, butene, pentene, hexene, heptene, octene, 2-methylpropene-1, 3-methylbutene-1, 4-methylpentene-1, 4-methylhexene -1,5-methylhexene-1, bicyclo-(2.2.1)-2-heptene, butadiene, pentadiene, hexadiene, isoprene, 2,3-dimethylbutadiene-1,3, 2-methylpentadiene-1,3, 4-vinylcyclohexene, vinylcyclohexene, cyclopentadiene, styrene and methylstyrene, and the like.

Other polymers in addition to the above-described olefin polymers that are useful in the invention include polyindene, indenecoumarone resins; polymers of acrylate esters and polymers of methacrylate esters, acrylate and methacrylate resins such as ethyl acrylate, n-butyl methacrylate, isobutyl methacrylate, ethyl methacrylate and methyl methacrylate; alkyd resins and paint vehicles, such as bodied linseed oil; cellulose derivatives such as cellulose acetate, cellulose acetate butyrate, cellulose nitrate, ethyl cellulose, hydroxyethyl cellulose, methyl cellulose and sodium carboxymethyl cellulose; epoxy resins: furan resins (furfuryl alcohol or furfuralketone); hydrocarbon resins from petroleum; isobutylene resins (polyisobutylene); isocyanate resins (polyurethanes); melamine resins such as melamine-formaldehyde and melamine-urea-formaldehyde; oleoresins; phenolic resins such as phenol-formaldehyde, phenolic-elastomer, phenolic-epoxy, phenolic-polyamide, and phenolic-vinyl acetals; polyamide polymers, such as polyamides, polyamide-epoxy and particularly long chain synthetic polymeric amides containing recurring carbonamide groups as an integral part of the main polymer chain; polyester resins such as polyesters of dibasic acids and dihydroxy compounds, and polyester elastomer and resorcinol resins such as resorcinol-formaldehyde, resorcinol-furfural, resorcinol-phenol-formaldehyde, resorcinol-polyamide and resorcinol-urea; rubbers such as natural rubber, synthetic polyisoprene, reclaimed rubber, chlorinated rubber, polybutadiene, cyclized rubber, butadiene-acrylonitrile rubber, butadiene-styrene rubber, and butyl rubber; neoprene rubber (polychloroprene); polysulfides (Thiokol); terpene resins; urea resins; vinyl resins such as polymers of vinyl acetal, vinyl acetate or vinyl alcohol-acetate copolymer, vinyl alcohol, vinyl chloride, vinyl butyral, vinyl chloride-acetate copolymer, vinyl pyrrolidone and vinylidene chloride copolymers; polyformaldehyde; polyphenylene oxide; polymers of diallyl phthalates and phthalates; polycarbonates of phosgene or thiophosgene and dihydroxy compounds such as bisphenols, phosgene, thermoplastic polymers of bisphenols and epichlorohydrin (trade named Phenoxy polymers); graft copolymers and polymers of unsaturated hydrocarbons and unsaturated monomer, such as graft copolymers of polybutadiene, styrene and acrylonitrile, commonly called ABS resins; ABS polyvinyl chloride polymers, recently introduced under the trade name of Cycovin; and acrylic polyvinyl chloride polymers, known by the trade name Kydex 100.

The compounds of this invention have been found to have particular utility in thermoplastic resin systems, such as polyethylene, polypropylene, polybutylene, polystyrene, polyacrylates, nylon and polybutadiene systems. Particular utility is also found in copolymer or blended resin systems, such as high impact polystyrene, styrene-acrylonitrile, ABS, styrene-butadiene, blends of polystyrene and polyphenylene oxide, and, saturated polyester polyethylene and polybutylene terephthalate.

The compounds of this invention have been found to have particular utility in thermosetting resin systems, such as phenol-formaldehyde, unsaturated polyester, and epoxy resin system.

The polymers of the invention can be in various physical forms, such as shaped articles, for example, moldings, sheets, rods, and the like; fibers, coatings, films and fabrics, and the like.

It should be noted that it is also within the scope of the present invention to incorporate such ingredients as plasticizers, dyes, pigments, stabilizers, antioxidants, antistatic agents and the like to the novel composition.

In all the examples of the application of the products of the invention to textile materials the following general procedure was used except when otherwise specifically noted.

Padding was done on a standard two roll laboratory padder at a gauge pressure of 60 pounds per square inch in all cases. Drying and curing during processing were done with a standard laboratory textile circulating air oven. Washing and drying was done in standard home top loading automatic washer and dryer. Flammability testing was done in accordance with the American Association of Textile Chemists and Colorist Test Method 34-1969, the standard vertical char method.

Therein 2 ¾ in. × 10 in. fabric test specimens are exposed to a controlled burner flame under controlled conditions for a period of 12.0 seconds and 3.0 seconds. The charred specimens are thereafter subjected to controlled tearing tests, using tabulated weights, and the average tear length is measured as representing the char length of the flame retardant treated fabric. For comparison purposes, it should be noted that untreated fabric samples used in the examples of this case would be consumed in the test.

ASTM Test D2863-70, used in accordance with the following examples, generally provides for the comparison of relative flammability of self-supporting plastics by measuring the minimum concentration of oxygen in a slowly rising mixture of oxygen and nitrogen that will support combustion. The procedure encompasses supporting cylindrical test specimens 70–150 mm × 8 mm vertically in a glass tube fitted with controlled upward oxygen/nitrogen gas flow. The top of the specimen is ignited and oxygen flow is adjusted until it reaches that minimum rate at which the specimen is extinguished before burning 3 minutes or 50 mm whichever happens first. The oxygen index(n) is then calculated as follows:

$$n,\% = (100 \times O_2)/(O_2+N_2)$$

wherein $O_2$ is the volumetric flow of oxygen, at the minimal rate and $N_2$ is the corresponding volumetric flow rate of nitrogen.

A modification of ASTM Test D635-68 is used in accordance with the following examples, generally provides for the comparison of burning rates, self-extinguishment and non-burning characteristics of plastics in the form of sheets, bars, plates or panels. The procedure encompasses preparing 150 × 8 mm cylindrical samples with and without the subject flame retardant additive. Each sample is marked at points 1 inch and 4 inches from its end and held, marked end in the flame, at a 45° angle in a controlled burner flame (1 inch flame length) for two 30 second attempts. The movement of the flame up the length of the sample through the two points is measured for rate of burning, non-burning or self-extinguishing characteristics. A sample is rate SE(self-extinguishing) if the flame burns through the first point but extinguishes before reaching the second point. A sample is rated NB(non-burning) if, upon ignition it does not burn to the first point.

The following examples are set forth for purposes of illustration only and are not to be construed as limitations of the present invention except as set forth in the appended claims. All parts and percentages are by weight unless otherwise specified.

EXAMPLE I

Preparation of

A 250 ml. flask, fitted with a reflux condenser, mechanical stirrer and thermometer, was charged with 83g. (0.5 mole) triethyl phosphite and was heated to 100° C. 73.2g. (0.4 mole) of diethyl phosphoramidate was added to the flask over a period of 15 minutes and the reaction mixture was thereafter heated at 115° C for 2 hours. After cooling the reaction mixture was stripped, at 70° C under a reduced pressure of 0.5 mm mercury, to give 109g. of a pale yellow liquid. Infrared and nuclear magnetic resonance spectroscopy confirmed the structure to be essentially pure.

EXAMPLE II

Preparation of

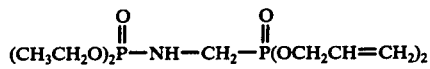

A 250 ml. flask was charged with 18.3g. (0.1 mole) of N-hydroxymethyl diethylphosphoramidate and 20.2g. (0.1 mole) of triallyl phosphite. The reaction mixture was heated at 120° C for 2 hours, then stripped under a vacuum of 2 mm mercury at 120° C to give 32.5g. of a pale yellow liquid. Infrared and nuclear magnetic resonance spectroscopy confirmed the structure and showed the product to be essentially pure.

EXAMPLE III

Preparation of

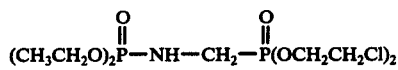

A 250 ml. flask was charged with 18.3g. (0.1 mole) of N-hydroxymethyl diethylphosphoramidate and 27g. (0.1 mole) of tris-2-chloroethyl phosphite. The reaction mixture was heated at 120° C for 2 hours, then stripped at 120° C under a reduced pressure of 2 mm mercury to yield 39g. of a clear liquid. This product was shown, by infrared and nuclear magnetic resonance spectroscopy, to be essentially pure.

EXAMPLE IV

Preparation of

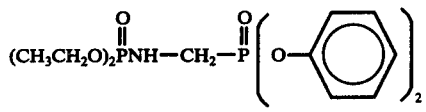

A mixture of 31g. (0.1 mole) of triphenyl phosphite and 18.3g. of N-hydroxymethyl diethylphosphoramidate was heated at about 130° C for about 5 hours in a round bottomed flask. The mixture was then stripped at about 120° C and about 22 mm pressure for about 2 hours to remove all volatiles. The resulting product, a viscous oil, was obtained in quantitative yield. The structure was confirmed by elemental and spectroscopic analysis to be substantially pure desired product.

EXAMPLE V

Preparation of

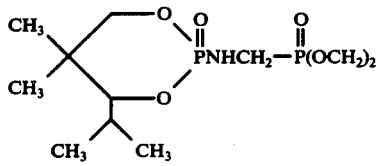

N-hydroxymethyl-(1-isopropyl-2,2-dimethyl)-1, 3 propylidenyl phosphoramidate, 59.3g. (0.25 mole) was mixed with 37g. (0.3 mole) of trimethyl phosphite and 80 ml. diglyme in a 250 ml. flask. The reaction mixture was slowly heated to 115° C and held at this temperature for 15 hours. After cooling, volatile material was removed from the reaction mixture by stripping under a vacuum of about 1 mm. mercury. 70g. of product, a viscous oil, was obtained which, under infrared and nuclear resonance spectroscopy, was shown to be essentially pure desired product.

EXAMPLE VI

To 70 parts of polypropylene was added 30 parts of N-(diethylphosphonomethyl) diethylphosphoramidate and dry blended for about five minutes. The resulting mixture was then brought to a melt and thoroughly mixed for about 15 minutes. After cooling the resulting solid was cut into small pieces and added slowly to a 9 mm glass tube immersed in a hot salt bath. The temperature of the salt bath is maintained above the melt temperature of the polymer mixture added. After all the pieces had been melted a steel rod with a weight attached is placed in the glass rod and the mixture allowed to cool. The resulting rod of polymer and additive (150–200 mm. length) is then removed and tested by modified ASTM Tests D2863-70 and D635-68 as previously described. The test results are set forth in Table I below.

EXAMPLES VII-XIV

Various phosphonates are mixed with polymers in the preparations and according to the process of Example 6. Testing under modified ASTM Tests D2863-70 and D635-68 are recorded in Table I.

EXAMPLES XV-XXI

Various polymers are treated by the process of Example 6 with the exception that no phosphate additives are mixed therewith. Test results thereof are recorded in Table I.

TABLE I

| Example | Additive | Polymer | Flammability Tests | | Percent Additive |
|---|---|---|---|---|---|
| | | | Oxygen Index | D-635 | |
| VI | (CH$_3$CH$_2$O)$_2$P(O)—NH—CH$_2$—P(O)(OCH$_2$CH$_3$)$_2$ | Polypropylene | 23.2 | NB | 30 |
| VII | (CH$_3$CH$_2$O)$_2$P(O)—NH—CH$_2$—P(O)(OCH$_2$CH$_2$Cl)$_2$ | Polystyrene | 23.0 | NB | 30 |
| VIII | (CH$_3$CH$_2$O)$_2$P(O)—NH—CH$_2$—P(O)(OCH$_2$CH=CH$_2$)$_2$ | ABS | 24.3 | NB | 30 |
| IX | (CH$_3$CH$_2$O)$_2$P(O)—NH—CH$_2$—P(O)(Oϕ)$_2$ | Epoxy | 27.2 | NB | 30 |
| X | [cyclic phosphoramidate structure]—P—NH—CH$_2$—P(O)(OCH$_3$)$_2$ | Polypropylene | 19.8 | NB | 30 |
| XI | " | ABS | 22.0 | NB | 30 |
| XII | " | Nylon | 29.0 | NB | 30 |
| XIII | " | Polyethylene terephthalate | 25.0 | NB | 30 |
| XIV | " | SBR | 24.8 | NB | 30 |
| XV | | Polypropylene | 17.4 | B | |
| XVI | | Polystyrene | 18.0 | B | |
| XVII | | ABS | 19.0 | B | |
| XVIII | | Nylon | 22.1 | SE | |
| XIX | | Polyethylene terephthalate | 22.7 | B | |
| XX | | Epoxy | 22.5 | B | |
| XXI | | SBR | 19.6 | B | |

EXAMPLE XXII

N-(Diethylphosphonomethyl)-diethylphosphoroamidate, 60g was dissolved in 200 ml of water containing 1.1 molar equivalents of formaldehyde. The pH was adjusted to 10.0 with 50% sodium hydroxide solution and the mixture stirred for three hours at about 50° C. The mixture was then cooled to room temperature and the pH adjusted to 7.0 with hydrochloric acid. Trimethylol melamine, 20g. was added with 5.0g of ammonium chloride.

A sample of 5.0 oz. per square yard cotton sheeting was immersed in the above solution and padded through a two roll laboratory padder, at about 60 lb per sq. in. gauge pressure, to give a wet pick-up of about 92%. The sample was dried in a circulating air oven for about 2.0 minutes at about 250° F and then cured for about 4.0 minutes at about 350° F. The sample was then washed in an automatic washer using Tide as the detergent, and tumble dried. Flame retardancy was then determined by the standard vertical char test AATCC D34-1969 and oxygen index test ASTM D2863-70. The weight add-on was 22.3%.

Durability to washing was determined by washing the sample through one cycle of an automatic washer using Tide as the detergent.

The results are contained in Table II. Therein B indicates the sample burns so that char length was non determinable, and SE indicated the sample self-extinguished.

EXAMPLE XXIII

N-(Diallylphosphonomethyl)diethylphosphoroamidate 40g was mixed with 60g of formalin (40%) solution and stirred overnight at room temperature at a pH of 8.5-9.5. The pH was adjusted to 7.0 with hydrochloric acid and 23g of a 50% solution of trimethylolmelamine added along with 5g of NH$_4$Cl.

A sample of rayon staple fiber was immersed in the solution and excess solution removed by passing through a two roll padder at about 60 lb. gauge pressure to give a wet pick-up of about 100%. The sample was then dried about 2.5 minutes at about 250° F and cured for about 5.0 minutes at about 350° F in a circulation air oven. The sample was washed by hand in a water detergent mixture for 3 minutes and then dried. Flammability was determined by holding an end of the fiber in a bunson flame for approximately 2 sec. and withdrawing.

Durability was determined by washing the samples in a cotton bag in an automatic washer with Tide in a standard home wash cycle. The sample was then tumble dried and tested as above. Results of these tests and tests for other compositions on rayon are shown in Table II.

EXAMPLE XXIV

N-(Bis-betachloroethylphosphonomethyl)-diethylphosphoramidate, 30g, was mixed with 45g of formalin solution (40%) and stirred overnight at a pH of 10. The pH was adjusted to 7.0 with hydrochloric acid and 5g of ammonium chloride and 17g of a 50% solution of trimethylolated melamine added.

A sample of 6.0 oz. sq. yd. of wool was padded through the above solution and the excess squeezed out by passing through a two roll laboratory padder at about 60 lb. sq. in. gauge pressure. The sample was then dried at about 250° F for about 2 minutes and cured at about 350° F for about 4 minutes. The sample was then given a standard home wash, i.e. one cycle in a standard home type automatic washer using "Tide" detergent. Flame retardancy was determined by the oxygen index and standard vertical char tests. The results thereof are contained in Table II.

EXAMPLE XXV

N-(Dimethylphosphonomethyl)-1,3-(1-isopropyl-2,2-dimethyl) propylidenyl phosphoramidate (40g.) was mixed with 60g. of formalin (40%) solution and stirred overnight at room temperature at a pH of 10. The pH was adjusted to 7.0 with hydrochloric acid and 23g. of a 50% solution of trimethylol melamine added, along with 5g. of NH$_4$Cl. Thereafter rayon staple fiber was padded and treated in accordance with Example XXIII. Test results are shown in Table II.

We claim:

1. An article comprising a resin composition and a flame retardant amount of a compound of the formula

wherein R' is phenyl, lower alkenyl and halogen substituted and unsubstituted lower alkyl of 1-6 carbon atoms, $m$ is an integer from 1-2 wherein when $m$ is 2, R is alkoxy of 1-8 carbon atoms and when $m$ is 1, R is alkylene dioxy of 2-8 carbon atoms.

2. The article of claim 1 wherein the compound is of the formula

3. The article of claim 1 wherein the compound is of the formula

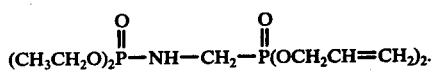

4. The article of claim 1 wherein the compound is of the formula

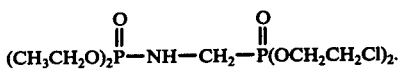

5. The article of claim 1 wherein the compound is of the formula

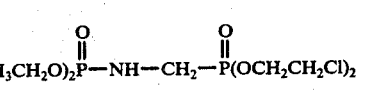

TABLE II

| Example | Compound | Textile | Percent Wet Pickup | Percent Add-on | Flammability Testing Initial | Home Wash | Initial OI |
|---|---|---|---|---|---|---|---|
| XXII | (CH$_3$CH$_2$O)$_2$P(=O)—NH—CH$_2$—P(=O)(OCH$_2$CH$_3$)$_2$ | Cotton | 92 | 22.3 | 3.7 in. | 4.1 in. | 24.3 |
| XXIII | (CH$_3$CH$_2$O)$_2$P(=O)—NH—CH$_2$—P(=O)(OCH$_2$CH=CH$_2$)$_2$ | Rayon | 100 | 13.8 | SE | SE | 25.0 |
| XXIV | (CH$_3$CH$_2$O)$_2$P(=O)—NH—CH$_2$—P(=O)(OCH$_2$CH$_2$Cl)$_2$ | Wool | 126 | 36.6 | 3.2 in. | 3.8 in. | 28.5 |
| XXV | (see structure) | Rayon | 106 | 23 | SE | SE | 24.7 |

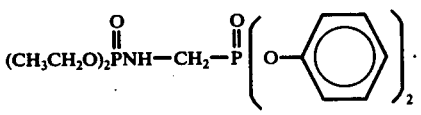

6. The article of claim 1 wherein the compound is of the formula

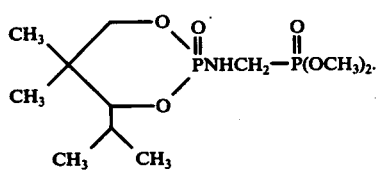

7. A process for rendering resin compositions flame retardant which comprises applying to said resin a flame retardant amount of a compound of the formula

wherein R' is phenyl, lower alkenyl and halogen substituted and unsubstituted lower alkyl of 1-6 carbon atoms, $m$ is an integer from 1-2 wherein when $m$ is 2, R is alkoxy of 1-8 carbon atoms and when $m$ is 1, R is alkylene dioxy of 2-8 carbon atoms.

8. The process of claim 7, wherein said resin composition is a thermoplastic resin composition.

9. The process of claim 8 wherein said thermoplastic resin composition is selected from the group consisting of polyethylene, polypropylene, polybutylene, polystyrene, polyacrylates, nylon and polybutadiene systems.

10. The process of claim 8 wherein said thermoplastic resin composition is a system selected from the group consisting of high impact polystyrene, styrene-acrylonitrile, acrylonitrile-butadiene-styrene, styrene-butadiene, blends of polystyrene and polyphenylene oxide, and, saturated polyester polyethylene and polybutylene terephthalate.

11. The process of claim 7 wherein said resin composition is a thermosetting resin composition.

12. The process of claim 11 wherein said thermosetting resin composition is selected from the group consisting of phenol-formaldehyde, unsaturated polyesters, and epoxy resin systems.

* * * * *

UNITED STATES PATENT AND TRADEMARK OFFICE
CERTIFICATE OF CORRECTION

PATENT NO. : 4,053,450
DATED : October 11, 1977
INVENTOR(S) : Peter Golborn and James J. Duffy It is certified that error appears in the above-identified patent and that said Letters Patent are hereby corrected as shown below:

Column 2, line 35, "halogen unsubstituted lower alkyl" should read --halogen substituted and unsubstituted lower alkyl--.

Signed and Sealed this

Sixteenth Day of May 1978

[SEAL]

Attest:

RUTH C. MASON
Attesting Officer

LUTRELLE F. PARKER
Acting Commissioner of Patents and Trademarks